US012715835B2

(12) United States Patent
Huber et al.

(10) Patent No.: US 12,715,835 B2
(45) Date of Patent: Aug. 25, 2026

(54) BIORENEWABLE SYNTHESIS OF HYDROXY-HEXANOATE ESTERS

(71) Applicant: Wisconsin Alumni Research Foundation, Madison, WI (US)

(72) Inventors: George Huber, Middleton, WI (US); Marco Nazareno Dell Anna, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 571 days.

(21) Appl. No.: 18/365,645

(22) Filed: Aug. 4, 2023

(65) Prior Publication Data

US 2024/0308950 A1 Sep. 19, 2024

Related U.S. Application Data

(60) Provisional application No. 63/395,619, filed on Aug. 5, 2022.

(51) Int. Cl.

*C07C 67/03* (2006.01)
*B01J 21/18* (2006.01)
*B01J 23/44* (2006.01)
*C07C 67/333* (2006.01)

(52) U.S. Cl.

CPC ............... *C07C 67/03* (2013.01); *B01J 21/18* (2013.01); *B01J 23/44* (2013.01); *C07C 67/333* (2013.01)

(58) Field of Classification Search

CPC ..... C07C 67/03; C07C 67/333; C07C 69/675; B01J 21/18; B01J 23/44; B01J 23/755; B01J 23/16; B01J 23/462; B01J 23/464; B01J 23/48; B01J 23/42

See application file for complete search history.

(56) References Cited

U.S. PATENT DOCUMENTS 4,668,433 A 5/1987 Ochsner

FOREIGN PATENT DOCUMENTS

CN 110803989 A 2/2020
CN 113292525 A 8/2021

OTHER PUBLICATIONS

Nanduri, v. b., et al., Biochemical approaches to the synthesis of ethyl 5-(S)-hydroxyhexanoate and 5-(S)-hydroxyhexanenitrile, Enzyme and Microbial Technology, vol. 28, pp. 632-636 (Year: 2001).*
Bacardit, R., et al., Hydrogenation of triacetic acid lactone. A new synthesis of the carpenter bee (Xylocopa hirsutissima) sex pheromone, Terahedron Letters, vol. 21, pp. 551-554 (Year: 1980).*
Barcardit et al. (1980) Tetrahedron Lett. 21: 551.
Huck et al. (2003) J. Catal. 219:41.
Richardson M. T. et al. Metab. Eng. 1999, 1, 180.
Xie D.M. et al. Biotech. Bioeng. 2006, 93, 727.
Zha W. et al. JACS, 2004, 126, 4534.

* cited by examiner

*Primary Examiner* — Yate' K Cutliff

(74) *Attorney, Agent, or Firm* — Joseph T. Leone; Yanjun Ma; DeWitt LLP

(57) ABSTRACT

A method to make mono- or di-hydroxy-hexanoates. Triacetic acid lactone is converted to a δ-hexalactone or a 4-hydroxy-δ-hexalactone intermediate. The intermediate is treated with an acid in the presence of an alcohol to yield a 5-hydroxy-hexanoate or 4,5-dihydroxy-hexanoate.

19 Claims, 2 Drawing Sheets

5-hydroxyhexanoate 5-hydroxyhexanoate 4,5-hydroxyhexanoate

BIORENEWABLE SYNTHESIS OF HYDROXY-HEXANOATE ESTERS

CROSS-REFERENCE TO RELATED APPLICATIONS

Priority is hereby claimed to provisional application Ser. No. 63/395,619, filed Aug. 5, 2022, which is incorporated herein by reference.

FEDERAL FUNDING STATEMENT

This invention was made with government support under DE-SC0018420 awarded by the US Department of Energy. The government has certain rights in the invention.

BACKGROUND

Esters are used extensively in a wide variety of industries. Among these industries are personal care products (where esters are used as emollients, solvents, thickening agents, surfactants, and fragrances) and the food industry (where esters are used as flavors, fragrances, and additives). Esters also find use in lubricants, pharmaceuticals, paints and coatings, surfactants and detergents, and in other industries. The demand for esters is especially robust in the food, skin care, and cosmetics industries. Alkyl esters are widely known for their distinct, earthy, woody, or fruity fragrance. Ethyl hexanoate, for example, has a very distinct pineapple fragrance, while pentyl hexanoate has a distinct apple fragrance. Longer alkyl hexanoates (for example hexyl, heptyl, octyl, and benzyl hexanoates) have a minty or earthy fragrance. Hydroxy-substituted esters likewise have distinct flavors and fragrances.

Conventionally, terminal hydroxy-esters are made via the Baeyer-Villager oxidation. The Baeyer-Villager oxidation itself yields a lactone from a cyclic ketone. The lactone can then be ring-opened to yield the corresponding hydroxy ester. For example, starting from cyclohexane yields ethyl-5-hydroxypentanoate:

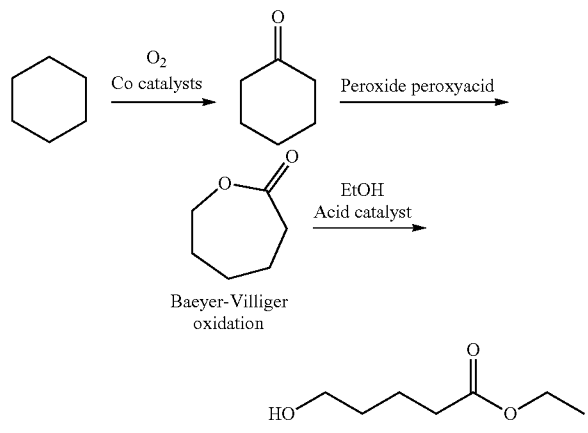

Here, cyclohexane is oxidized to cyclohexanone, a cyclic ketone. The Baeyer-Villager oxidation is then brought to bear to yield caprolactone. The caprolactone is then ring-opened to yield the corresponding terminal-hydroxy ester, in this case ethyl-5-hydroxypentanoate.

More complex hydroxy-substituted esters can be made using literature methods. See, for example, U.S. Pat. No. 4,668,433, issued May 26, 1987, to Ochsner, which describes derivatives of 6-hydroxyhexanoates having the following structure:

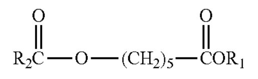

$R_1$ can be $C_1$ to $C_4$ alkyl or $C_2$ to $C_4$ alkenyl and $R_2$ can be, among other substituents, methoxy or ethoxy. These esters are made by treating an alcohol having the formula

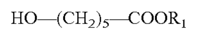

$$HO—(CH_2)_5—COOR_1$$

with an acylating agent such as an acyl halide or an acid anhydride.

See also CN 110803989, which describes a method to make ethyl-3-hydroxyhexanoate. Here, ethyl acetate is reacted bromine to yield ethyl bromoacetate. The ethyl bromoacetate is then reacted with n-butyl aldehyde to yield ethyl 3-hydroxycaproate:

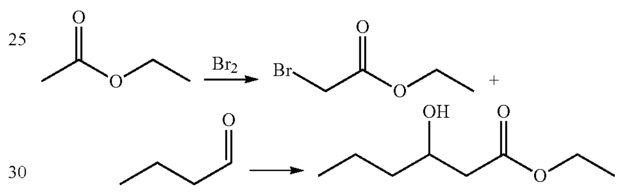

Another route to hydroxy-substituted esters is described in published Chinese patent application CN113292525. This published application describes a method to make delta caprolactone, which can then be ring-opened to the corresponding hydroxy-substituted ester. The method includes the steps of dissolving a beta-dicarbonyl compound and a base catalyst in a solvent and then dripping acrylic acid alkyl ester into the reaction to drive a Michael addition reaction. The reaction is then cooled and a base is added. Heating the mixture causes saponification. A reducing agent is then added to drive cyclization into delta caprolactone:

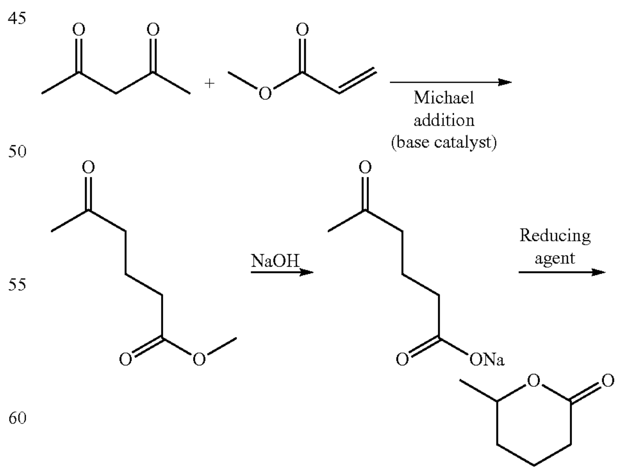

The delta caprolactone can then be ring-opened into the corresponding hydroxy-substituted ester.

The above-noted conventional routes to hydroxy-substituted esters, however, all begin with a petroleum-derived reactant. Thus, there remains a long-felt and unmet need for a simplified, streamlined method to make hydroxy-substituted hexanoate esters from renewable sources.

SUMMARY OF THE INVENTION

Disclosed herein is a method to make mono- or dihydroxy-hexanoates. The method comprises converting triacetic acid lactone to a δ-hexalactone and/or a 4-hydroxy-δ-hexalactone intermediate. The intermediate is then treated with an acid in the presence of an alcohol to yield a 5-hydroxy-hexanoate and/or 4,5-dihydroxy-hexanoate.

In another version of the method, triacetic acid lactone is hydrogenated to 4-hydroxy-δ-hexalactone. The 4-hydroxy-δ-hexalactone is then treated with an acid in the presence of an alcohol to yield a 4,5-dihydroxy-hexanoate product. Similarly, the 4-hydroxy-δ-hexalactone is converted to δ-hexalactone. The δ-hexalactone is then treated with an acid in the presence of an alcohol to yield a 5-hydroxy-hexanoate product.

In a preferred version of the method, the alcohol is R—OH, wherein R is selected from the group consisting of substituted or unsubstituted $C_1$ to $C_{12}$ alkyl, substituted or unsubstituted $C_2$ to $C_{12}$-alkenyl, substituted or unsubstituted $C_2$ to $C_{12}$-alkynyl, substituted or unsubstituted $C_3$ to $C_{12}$ cycloalkyl, substituted or unsubstituted $C_4$ to $C_{12}$ cycloalkenyl, or substituted or unsubstituted aryl.

The acid used in the method may be a homogeneous acid or a solid acid catalyst.

The hydrogenation steps are preferably conducted using $H_2$ under pressure in the presence of a catalyst comprising a primary metal selected from the group consisting of Ni, Nb, Co, Cu, Fe, Ru, Rh, Pd, Ag, Os, Ir, Pt, or Au.

Abbreviations and Definitions

In general, “substituted” refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., Cl. F, Br, and I); hydroxyls; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-, 2,5- or 2,6-disubstituted cyclohexyl groups, which may be substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, $-CH{=}CH(CH_3)$, $-CH{=}C(CH_3)_2$, $-C(CH_3){=}CH_2$, $-C(CH_3){=}CH(CH_3)$, $-C(CH_2CH_3){=}CH_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to $-C{\equiv}CH$, $-C{\equiv}CCH_3$, $-CH_2C{\equiv}CCH_3$, $-C{\equiv}CCH_2CH(CH_2CH_3)_2$, among others. Representative substituted alkynyl groups may be monosubstituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

The term "ester" as used herein refers to —C(=O)OR groups, in which R is a substituted or unsubstituted alkyl, cycloalkyl, alkenyl, alkynyl, aryl, aralkyl, heterocyclylalkyl or heterocyclyl group as defined herein.

"TAL" refers to "triacetic acid lactone," which is synonymous with "HMP," both of which refer to the renewable feed stock chemical 4-hydroxy-6-methyl-2-pyrone:

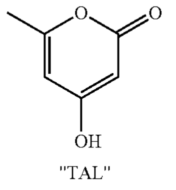

"TAL"

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the disclosed method shall include the corresponding plural characteristic or limitation, and vice-versa, unless otherwise specified or clearly implied to the contrary by the context in which the reference is made. The indefinite articles "a" and "an" mean "one or more."

All combinations of method steps disclosed herein can be performed in any order, unless otherwise specified or clearly implied to the contrary by the context in which the referenced combination is made.

The method disclosed herein can comprise, consist of, or consist essentially of the essential elements and steps described herein, as well as any additional or optional ingredients, components, or limitations described herein or otherwise useful in synthetic/enzymatic organic chemistry.

DETAILED DESCRIPTION OF THE INVENTION

Figure 1:
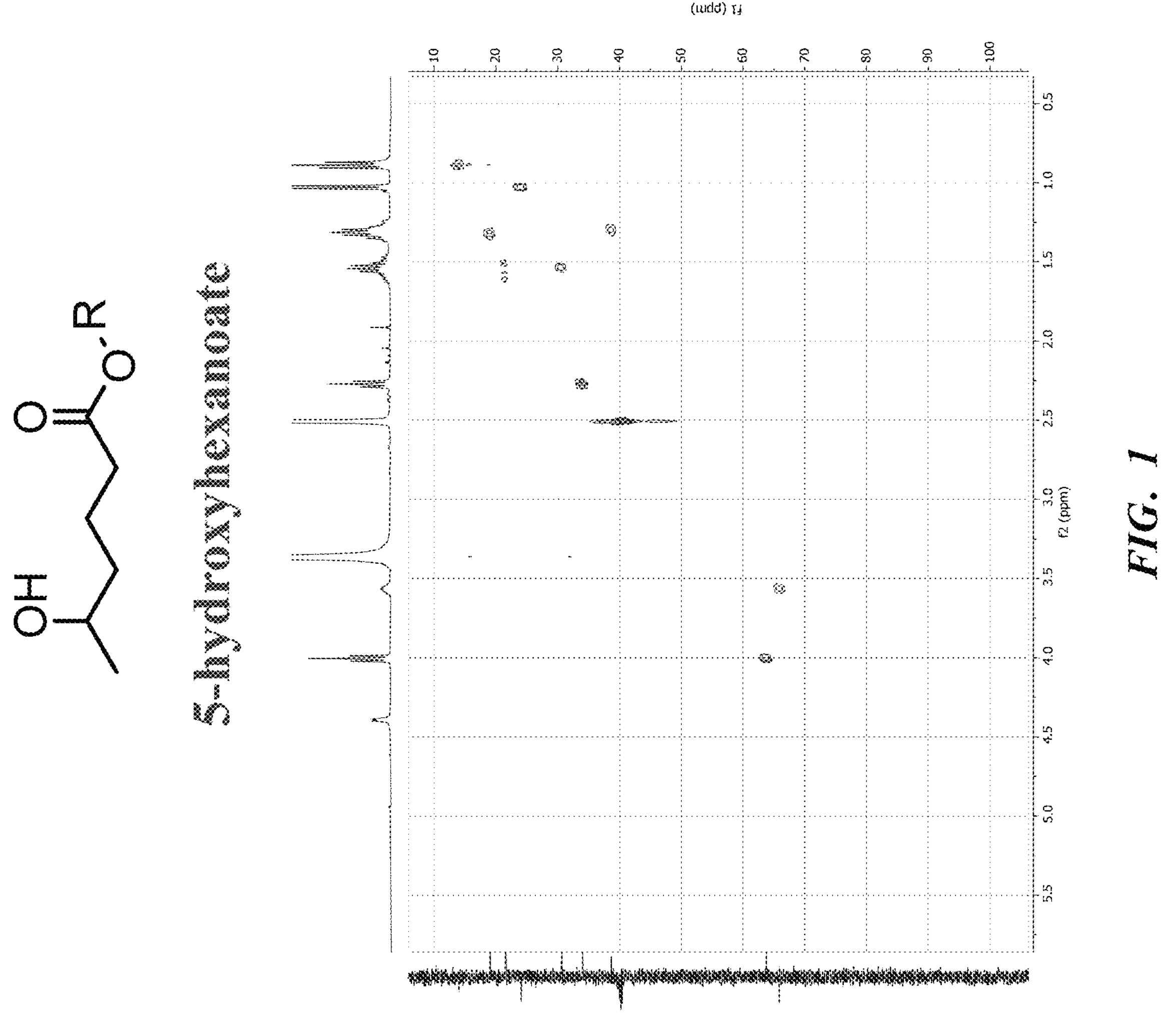
FIG. 1 is a 2-D NMR spectrum of ethyl-5-hydroxyhexanoate.

Disclosed herein is a method of making hydroxy-substituted hexanoate esters from the renewable feedstock TAL. TAL (i.e., triacetic acid lactone; 4-hydroxy-6-methyl-2-pyrone) is conventionally produced from acetic acid. However, it can be produced from sugars such as glucose using recombinant bacteria or yeast. See Xie D. M. et al. *Biotech. Bioeng.* 2006, 93, 727; Zha W. et al. *JACS* 2004, 126, 4534 and Richardson M. T. et al. *Metab. Eng.* 1999, 1, 180. This is important both economically and ecologically because the TAL precursor used in the present method can be fabricated de novo from renewable resources. Thus, the present method constitutes a bio-renewable platform from which hydroxy-substituted hexanoates can be derived.

In the first step of the method TAL is partially reduced to "C6" i.e. 4-hydroxy-δ-hexalactone. See Reaction Scheme 1:

Reaction Scheme 1-The present Method

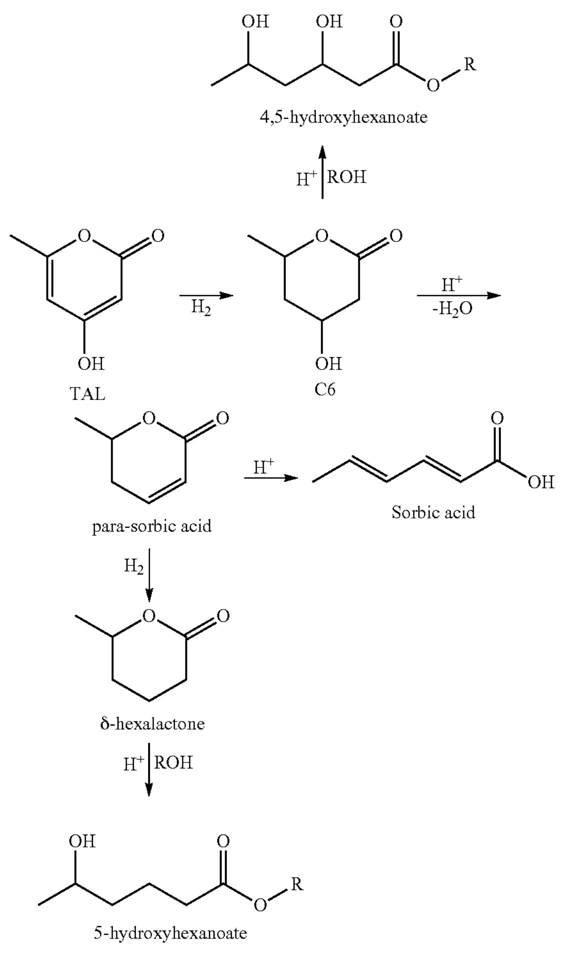

4,5-hydroxyhexanoate

TAL

C6 para-sorbic acid

Sorbic acid

δ-hexalactone 5-hydroxyhexanoate wherein R is substituted or unsubstituted $C_1$ to $C_{12}$ alkyl, substituted or unsubstituted $C_2$ to $C_{12}$-alkenyl, substituted or unsubstituted $C_2$ to $C_{12}$-alkynyl, substituted or unsubstituted $C_3$ to $C_{12}$ cycloalkyl, substituted or unsubstituted $C_4$ to $C_{12}$ cycloalkenyl, or substituted or unsubstituted aryl.

The partial hydrogenation of TAL to 5,6-dihydro-4-hydroxy-6-methyl-2H-pyran-2-one (not shown in Scheme 1):

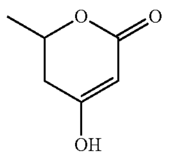

has been described in the literature, and can be accomplished either stereoselectively using Pd-based catalysts with chiral modifiers (Huck et al. (2003) *J. Catal.* 219:41), or non-stereoselectively using Pd- or Ni-based catalysts in alcohol solvents (Barcardit et al. (1980) *Tetrahedron Lett.* 21: 551). By carefully monitoring the reaction conditions, the hydrogenation reaction can be carried forward to yield "C6" as shown in Reaction Scheme 1, namely 4-hydroxy-δ-hexalactone. In the present method, stereoselectivity is not critical, so Pd- or Ni-based catalysts are preferred. Here, palladium-on-carbon (PdC) catalyst in butanol was used with great success. Yields of C6 from the TAL reactant were quantitative–100%. The partial hydrogenation reaction is preferably carried out at a temperature from about 300 to 400 K (26.8° C. to 126.8° C.), and a $H_2$ partial pressure from about 250 psi to 1000 psi. Lower alcohols are the preferred solvent, e.g., ethanol, propanol, butanol, etc., although carboxylic acids such as acetic acid may also be used as a solvent. Quantitative yield of the C6 intermediate was achieved when running the reaction at 50° C. and 507.6 psi (35 Bar) partial pressure of $H_2$. The catalyst ratio (10 wt % PdC to TAL; w/w)—was 1:2. The reaction was stirred at 750 rpm. Reaction time was 2 hours.

The method branches at C6. Moving upward in Reaction Scheme 1, the C6 intermediate was ring opened by treating it with a with an acid (either homogenous or a solid acid catalyst) in the presence of an alcohol, ROH. The "R" group is as defined hereinabove. This yields one type of desired esters, an R-4,5-dihydroxyhexanoate.

The solid acid catalysts for use in the method may comprise one or more solid acid materials without limitation, whether now known or developed in the future. The solid acid catalyst can be used independently or alternatively can be utilized in combination with one or more mineral acid or other types of catalysts. Exemplary solid acid catalysts which can be utilized include, but are not limited to, heteropoly acids, acid resin-type catalysts, meso-porous silicas, acid clays, sulfated zirconia, molecular sieve materials, zeolites, silica-alumina, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., ZrO2, SnO2, TiO2, etc.) which may optionally be doped with additional acid groups such as SO42- may also be used as solid acid catalysts.

Further examples of suitable solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. The functional group is generally of the sulfuric acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer copolymers which are solid acid catalysts. Nafion® is a registered trademark of E.I. du Pont de Nemours & Co.)

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

Preferred homogenous acids are mineral acids such as hydrochloric acid (HCl), nitric acid ($HNO_3$), phosphoric acid ($H_3PO_4$), sulfuric acid ($H_2SO_4$), boric acid ($H_3BO_3$), hydrofluoric acid (HF), hydrobromic acid (HBr), perchloric acid ($HClO_4$), and hydroiodic acid (HI). Other acids may also be used.

The hydrogenation reactions described herein are preferably carried out using a palladium-, nickel, and/or niobium-based catalyst. Other noble metal-containing catalysts in addition to palladium (i.e., Ru, Rh, Ag, Os, Ir, Pt, or Au) may also be used. The noble metals may be in elemental form or in the form of oxides, sulfides, nitrates, other salts, etc. They may also be alloyed or admixed with other metals, metal oxides, metal salts, etc. The noble metal-containing catalysts may optionally be disposed on a solid support such as carbon, titania, zirconia, alumina, and the like.

Alternatively, the C6 can be dehydrated to parasorbic acid. The preferred means to accomplish the dehydration is to use a solid acid catalyst. Any solid acid catalyst now known or developed in the future can be used. THF is the preferred solvent, although any suitable aprotic solvent may be used (other linear or cyclic ethers, dimethyl sulfoxide, dimethylformamide, dioxane, etc.). The reaction is preferably carried out at a temperature from about 300 K to about 500 K, more preferably from about 353.15 K to about 413.15 K (about 80° C. to about 140° C.). The reaction is also preferably carried out at increased pressure, about 100 to 500 psi of an inert gas —$N_2$, He, Ar, etc. Under these conditions, the dehydration reaction to parasorbic acid is quantitative.

If desired, the parasorbic acid may be ring-opened to sorbic acid. There are two very old literature precedents for ring-opening parasorbic acid to yield sorbic acid. See Fownes G. (1872), "A Manual of Elementary Chemistry, 11$^{th}$ Ed.," Henry C. Lea, Philadelphia, PA; and Roscoe H. E. (1890), "A Treatise on Chemistry, Vol. III," Macmillan & Co., New York, NY. In both literature precedents, the PSA was heated in the presence of KOH or HCl to yield sorbic acid.

Rather than driving the parasorbic acid to sorbic acid, in the present method the parasorbic acid is hydrogenated to δ-hexalactone (i.e., δ-caprolactone). As in the branch from C6 to R-4,5-dihydroxyhexanoate, the δ-hexalactone is treated with an acid (as defined hereinabove) in the presence of an alcohol, ROH. "R" is as defined previously. The resulting, desired product is a R-5-hydroxyhexanoate.

Figure 2:
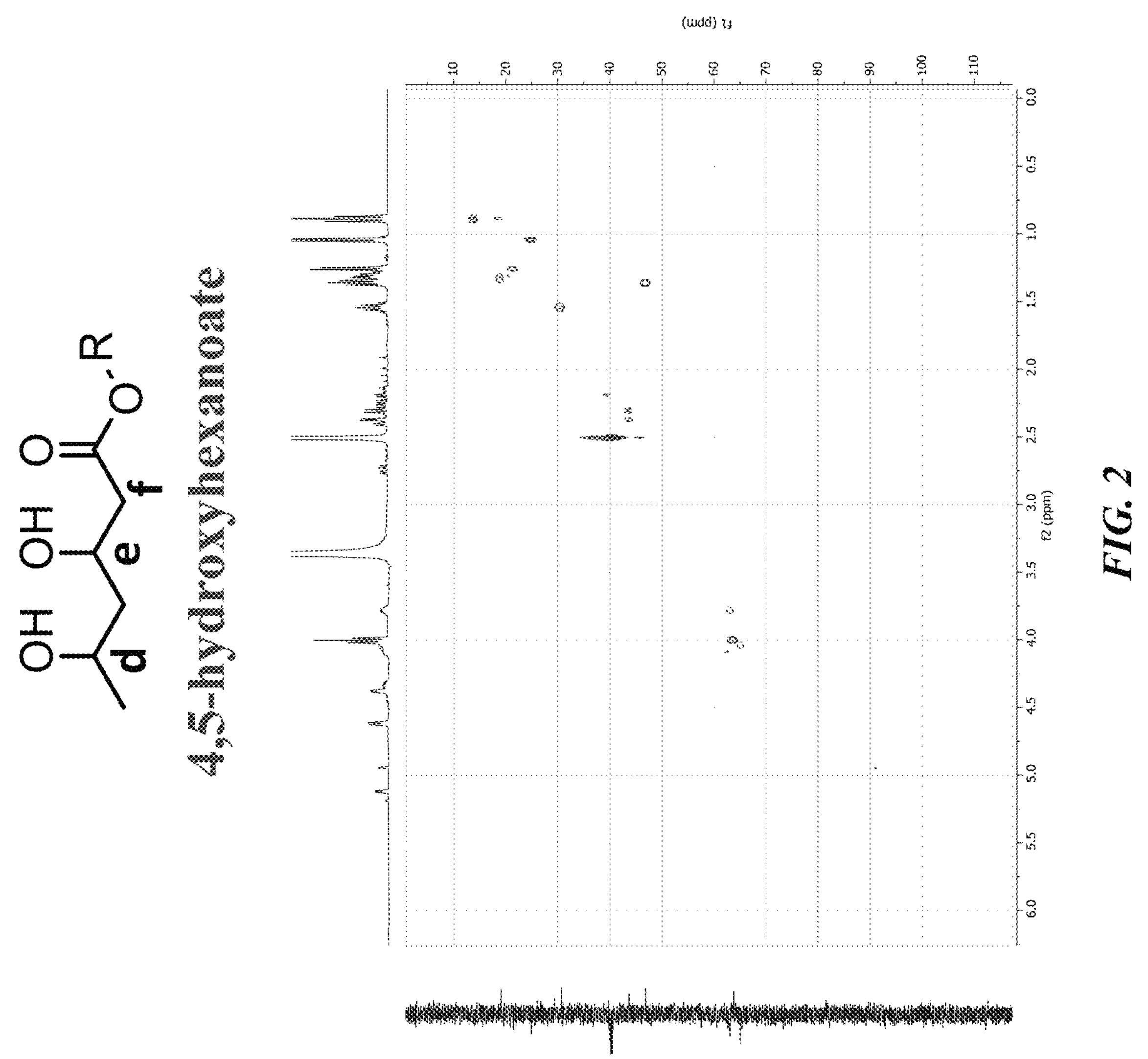
FIG. 2 is a 2-D NMR spectrum of ethyl-4,5-dihydroxyhexanoate.

The method as described has been used to make a host of hydroxy and di-hydroxy substituted hexanoates, including methyl, ethyl, propyl, butyl, pentyl, and hexyl 5-hydroxyhexanoate and methyl, ethyl, propyl, butyl, pentyl, and hexyl 4,5-dihydroxyhexanoate. These compounds and fragrances ranging from pineapple, to apple, to non-specific fruity, to buttery, to herbal. In terms of yields, for example, ethyl-5-hydroxyhexanoate was made using the present method in 56% yield. Butyl-5-hydroxyhexanoate was made in 80% yield. Hexyl-5-hydroxyhexanoate 72% yield (All yields from TAL.) NMR spectra for ethyl-5-hydroxyhexanoate and ethyl-4,5-dihydroxyhexanoate made using the present method are shown in FIGS. 1 and 2, respectively.

The invention claimed is:

1. A method to make mono- or di-hydroxy-hexanoates, the method comprising:

(a) converting triacetic acid lactone to δ-hexalactone and/or 4-hydroxy-δ-hexalactone; and (b) treating the δ-hexalactone and/or 4-hydroxy-δ-hexalactone with an acid in the presence of an alcohol to yield 5-hydroxy-hexanoate and/or 4,5-dihydroxy-hexanoate.

2. The method of claim 1, wherein in step (a), at least a portion of the triacetic acid lactone is hydrogenated into 4-hydroxy-δ-hexalactone; and in step (b), the 4-hydroxy-δ-hexalactone is treated with an acid in the presence of an alcohol such that at least a portion of the 4-hydroxy-δ-hexalactone is converted to 4,5-dihydroxy-hexanoate.

3. The method of claim 2, wherein the alcohol is R—OH, wherein R is selected from the group consisting of substituted or unsubstituted $C_1$ to $C_{12}$ alkyl, substituted or unsubstituted $C_2$ to $C_{12}$-alkenyl, substituted or unsubstituted $C_2$ to $C_{12}$-alkynyl, substituted or unsubstituted $C_3$ to $C_{12}$ cycloalkyl, substituted or unsubstituted $C_4$ to $C_{12}$ cycloalkenyl, or substituted or unsubstituted aryl.

4. The method of claim 3, wherein the acid is selected from homogeneous acids or solid acid catalysts.

5. The method of claim 2, wherein the acid is selected from homogeneous acids or solid acid catalysts.

6. The method of claim 2, wherein the hydrogenation is conducted in the presence of a catalyst comprising a metal selected from the group consisting of Ni, Nb, Ru, Rh, Pd, Ag, Os, Ir, Pt, and Au.

7. The method of claim 1, wherein in step (a), at least a portion of the triacetic acid lactone is hydrogenated into 4-hydroxy-δ-hexalactone; and in step (b), at least a portion of the 4-hydroxy-δ-hexalactone is converted to δ-hexalactone and the δ-hexalactone is treated with an acid in the presence of an alcohol such that at least a portion of the δ-hexalactone is converted to 5-hydroxy-hexanoate.

8. The method of claim 7, wherein the alcohol is R—OH, wherein R is selected from the group consisting of substituted or unsubstituted $C_1$ to $C_{12}$ alkyl, substituted or unsubstituted $C_2$ to $C_{12}$-alkenyl, substituted or unsubstituted $C_2$ to $C_{12}$-alkynyl, substituted or unsubstituted $C_3$ to $C_{12}$ cycloalkyl, substituted or unsubstituted $C_4$ to $C_{12}$ cycloalkenyl, or substituted or unsubstituted aryl.

9. The method of claim 8, wherein the acid is selected from homogeneous acids or solid acid catalysts.

10. The method of claim 7, wherein the acid is selected from homogeneous acids or solid acid catalysts.

11. The method of claim 7, wherein the hydrogenation is conducted in the presence of a catalyst comprising a metal selected from the group consisting of Ni, Nb, Ru, Rh, Pd, Ag, Os, Ir, Pt, and Au.

12. A method to make mono- or di-hydroxy-hexanoates, the method comprising:

(a) hydrogenating triacetic acid lactone to 4-hydroxy-δ-hexalactone in the presence of a catalyst comprising a metal selected from the group consisting of Ni, Nb, Ru, Rh, Pd, Ag, Os, Ir, Pt, and Au; and (b) treating the 4-hydroxy-δ-hexalactone with an acid in the presence of an alcohol such that at least a portion of the 4-hydroxy-δ-hexalactone is converted to 4,5-dihydroxy-hexanoate.

13. The method of claim 12, wherein the alcohol is R—OH, wherein R is selected from the group consisting of substituted or unsubstituted $C_1$ to $C_{12}$ alkyl, substituted or unsubstituted $C_2$ to $C_{12}$-alkenyl, substituted or unsubstituted $C_2$ to $C_{12}$-alkynyl, substituted or unsubstituted $C_3$ to $C_{12}$ cycloalkyl, substituted or unsubstituted $C_4$ to $C_{12}$ cycloalkenyl, or substituted or unsubstituted aryl.

14. The method of claim 13, wherein the acid is selected from homogeneous acids or solid acid catalysts.

15. The method of claim 12, wherein the acid is selected from homogeneous acids or solid acid catalysts.

16. A method to make mono- or di-hydroxy-hexanoates, the method comprising:

(a) hydrogenating triacetic acid lactone to 4-hydroxy-δ-hexalactone in the presence of a catalyst comprising a metal selected from the group consisting of Ni, Nb, Ru, Rh, Pd, Ag, Os, Ir, Pt, and Au; and; and (b) converting at least a portion of the 4-hydroxy-δ-hexalactone to δ-hexalactone; and (c) treating the δ-hexalactone with an acid in the presence of an alcohol such that at least a portion of the δ-hexalactone is converted to 5-hydroxy-hexanoate.

17. The method of claim 16, wherein the alcohol is R—OH, wherein R is selected from the group consisting of substituted or unsubstituted $C_1$ to $C_{12}$ alkyl, substituted or unsubstituted $C_2$ to $C_{12}$-alkenyl, substituted or unsubstituted $C_2$ to $C_{12}$-alkynyl, substituted or unsubstituted $C_3$ to $C_{12}$ cycloalkyl, substituted or unsubstituted $C_4$ to $C_{12}$ cycloalkenyl, or substituted or unsubstituted aryl.

18. The method of claim 17, wherein the acid is selected from homogeneous acids or solid acid catalysts.

19. The method of claim 16, wherein the acid is selected from homogeneous acids or solid acid catalysts.

* * * * *